United States Patent [19]
Erickson et al.

[11] Patent Number: 5,525,490
[45] Date of Patent: Jun. 11, 1996

[54] REVERSE TWO-HYBRID METHOD

[75] Inventors: James R. Erickson, Hercules; Scott Powers, Berkeley, both of Calif.

[73] Assignee: ONYX Pharmaceuticals, Inc., Richmond, Calif.

[21] Appl. No.: 218,933

[22] Filed: Mar. 29, 1994

[51] Int. Cl.$^6$ .............................. C12Q 1/02; C12N 15/81; C12N 15/11

[52] U.S. Cl. .................. 435/29; 435/254.21; 536/23.7

[58] Field of Search ............................ 435/240.1, 240.2, 435/172.3, 320.1, 254.2, 254.21, 29; 424/93.21; 935/62, 69; 536/23.7

[56] References Cited

PUBLICATIONS

"A Novel Genetic System To Detect Protein–protein Interactions", by Fields et al., *Nature*, vol. 340, Jul. 20, 1989. pp. 245–246.

"A Contingent Replication Assay for the Detection of Protein–protein Interactions in Animal Cells", by Vasavada et al., *Proc. Natl. Acad. Sci.*, vol. 88, pp. 10686–10690, Dec. 1991.

"Mammalian Ras Interacts Directly with the Serine/Threonine Kinase Raf", by Vojtek et al., *Cell*, vol. 74, pp. 205–214, Jul. 16, 1993.

*Primary Examiner*—James Martinell
*Attorney, Agent, or Firm*—Gregory Giotta; Tracy Dunn

[57] ABSTRACT

The reverse two-hybrid method has been designed to provide a practical and efficient means of utilizing yeast cell-based assays to screen for molecules that can inhibit protein-protein interactions of interest. Existing two-hybrid systems involve reconstitution in yeast of a transcriptional activator that drives expression of a "reporter" gene such as HIS3 or lacZ. Attempts to utilize these existing systems for drug discovery would necessarily involve screening for molecules that interfere with the transcriptional read-out, and would be subject to detecting any compound that non-specifically interfered with transcription. In addition, since currently used reporter genes encode long-lived proteins, the assay would have to be performed over a lengthy time period to allow for decay of the preexisting reporter proteins. Any compound that would be toxic to yeast over this time period would also score as a "hit". The reverse two-hybrid interaction will avoid both of these pitfalls by driving the expression of a relay gene, such as the GAL80 gene, which encodes a protein that binds to and masks the activation domain of a transcriptional activator, such as Gal4. The reporter genes, which will provide the transcriptional read-out (HIS3 or lacZ), are dependent upon functional Gal4 for expression. Only when the level of Gal80 masking protein is reduced by interfering with the two-hybrid interaction will Gal4 function as a transcriptional activator, providing a positive transcriptional read-out for molecules that inhibit the two-hybrid protein-protein interaction. An important feature of the reverse two-hybrid system is that the basal level and half-life of the relay protein, Gal80, can be fine-tuned to provide maximum sensitivity.

12 Claims, No Drawings

REVERSE TWO-HYBRID METHOD

TECHNICAL FIELD

The invention relates to methods and compositions for identifying agents which modify intermolecular association between two or more polypeptides. Agents which specifically inhibit such protein-protein interactions are suitable for use as commercial reagents, pharmaceuticals, and for modulating gene expression in a cell culture and/or animal, such as to increase or decrease the expression of a predetermined protein in the cell culture or animal, and the like.

BACKGROUND

Specific protein-protein interactions are fundamental to most cellular and organismal functions. Polypeptide interactions are involved in formation of functional transcription complexes, signal transduction pathways, cytoskeletal organization (e.g., microtubule polymerization), polypeptide hormone receptor-ligand binding, organization of multi-subunit enzyme complexes, and the like.

Investigation of protein-protein interactions under physiological conditions has been problematic. Considerable effort has been made to identify proteins that bind to proteins of interest. Typically, these interactions have been detected by using co-precipitation experiments in which an antibody to a known protein is mixed with a cell extract and used to precipitate the known protein and any proteins which are stably associated with it. This method has several disadvantages, such as: (1) it only detects proteins which are associated in cell extract conditions rather than under physiological, intracellular conditions, (2) it only detects proteins which bind to the known protein with sufficient strength and stability for efficient co-immunoprecipitation, and (3) it fails to detect associated proteins which are displaced from the known protein upon antibody binding. For these reasons and others, improved methods for identifying proteins which interact with a known protein have been developed.

Two-Hybrid Systems

One approach has been to use a so-called "two-hybrid" system to identify polypeptide sequences which bind to a predetermined polypeptide sequence present in a fusion protein (Chien et al. (1991) *Proc. Natl. Acad. Sci. (USA)* 88: 9578). This approach identifies protein-protein interactions in vivo through reconstitution of a transcriptional activator (Fields S and Song O (1989) *Nature* 340: 245), the yeast Gal4 transcription protein. The method is based on the properties of the yeast Gal4 protein, which consists of separable domains responsible for DNA-binding and transcriptional activation. Polynucleotides encoding two hybrid proteins, one consisting of the yeast Gal4 DNA-binding domain fused to a polypeptide sequence of a known protein and the other consisting of the Gal4 activation domain fused to a polypeptide sequence of a second protein, are constructed and introduced into a yeast host cell. Intermolecular binding between the two fusion proteins reconstitutes the Gal4 DNA-binding domain with the Gal4 activation domain, which leads to the transcriptional activation of a reporter gene (e.g., lacZ, HIS3) which is operably linked to a Gal4 binding site. Typically, the two-hybrid method is used to identify novel polypeptide sequences which interact with a known protein (Silver SC and Hunt SW (1993) *Mol. Biol. Rep.* 17: 155; Durfee et al. (1993) *Genes Devel.* 7; 555; Yang et al. (1992) *Science* 257: 680; Luban et al. (1993) *Cell* 73: 1067; Hardy et al. (1992) *Genes Devel.* 6; 801; Bartel et al. (1993) *Biotechniques* 14: 920; and Vojtek et al. (1993) *Cell* 74: 205). However, variations of the two-hybrid method have been used to identify mutations of a known protein that affect its binding to a second known protein (Li B and Fields S (1993) *FASEB J.* 7: 957; Lalo et al. (1993) *Proc. Natl. Acad. Sci. (USA)* 90: 5524; Jackson et al. (1993) *Mol. Cell. Biol.* 13; 2899; and Madura et al. (1993) *J. Biol. Chem.* 268: 12046). Two-hybrid systems have also been used to identify interacting structural domains of two known proteins (Bardwell et al. (1993) *med. Microbiol.* 8: 1177; Chakraborty et al. (1992) *J. Biol. Chem.* 267: 17498; Staudinger et al. (1993) *J. Biol. Chem.* 268: 4608; and Milne GT and Weaver DT (1993) *Genes Devel.* 7; 1755) or domains responsible for oligomerization of a single protein (Iwabuchi et al. (1993) *Oncogene* 8; 1693; Bogerd et al. (1993) *J. Virol.* 67: 5030). Variations of two-hybrid systems have been used to study the in vivo activity of a proteolytic enzyme (Dasmahapatra et al. (1992) *Proc. Natl. Acad. Sci. (USA)* 89: 4159). Alternatively, an *E. coli*/BCCP interactive screening system (Germino et al. (1993) *Proc. Natl. Acad. Sci. (U.S.A.)* 90: 933; Guarente L (1993) *Proc. Natl. Acad. Sci. (U.S.A.)* 90: 1639) can be used to identify interacting protein sequences (i.e., protein sequences which heterodimerize or form higher order heteromultimers).

Each of these two-hybrid methods rely upon a positive association between two Gal4 fusion proteins thereby reconstituting a functional Gal4 transcriptional activator which then induces transcription of a reporter gene operably linked to a Gal4 binding site. Transcription of the reporter gene produces a positive readout, typically manifested either (1) as an enzyme activity (e.g., β-galactosidase) that can be identified by a colorimetric enzyme assay or (2) as enhanced cell growth on a defined medium (e.g., HIS3). Thus, these methods are suited for identifying a positive interaction of polypeptide sequences, but are poorly suited for identifying agents or conditions which alter (e.g., inhibit) intermolecular association between two polypeptide sequences.

In part, this is because a failure to obtain expression of the reporter gene can result from many events which do not stem from a specific inhibition of binding of the two hybrid proteins. For example, a two-hybrid system using a reporter gene that stimulates growth under defined conditions theoretically can be used to screen for agents that inhibit the intermolecular association of the two hybrid proteins, but it will be difficult or impossible to discriminate agents that specifically inhibit the association of the two hybrid proteins from agents which simply inhibit cell growth. Thus, an agent which is cytotoxic to yeast (e.g., bleach, phenol, ketoconazole, cycloheximide) will prevent cell growth without specifically inhibiting the interaction of two hybrid proteins and will score falsely as a positive hit. Similarly, a conventional two-hybrid system using a lacZ reporter gene will falsely score general transcription or translation inhibitors (e.g., cycloheximide) as being inhibitors of two hybrid protein binding. Thus, two-hybrid systems that produce a positive readout contingent upon intermolecular binding of the two hybrid proteins are generally not suitable for screening for agents which inhibit binding of the two hybrid proteins.

Unfortunately, it would be desirable to have an efficient screening method for identifying compounds which specifically alter the intermolecular association between two known polypeptide sequences under physiological conditions. Present two-hybrid methods rely on a positive readout and do not afford a method for identifying binding inhibitors (or binding competitors) with satisfactory sensitivity and/or selectivity.

Thus, there is a need in the art for compositions and methods which can be used to efficiently identify agents that specifically alter the intermolecular association between two polypeptide sequences in vivo. The present invention fulfills these and other needs.

The references discussed herein are provided solely for their disclosure prior to the filing date of the present application. Nothing herein is to be construed as an admission that the inventors are not entitled to antedate such disclosure by virtue of prior invention. All publications and patent applications herein are incorporated by reference to the same extent as if each individual publication or patent application was specifically and individually indicated to be incorporated by reference.

SUMMARY OF THE INVENTION

The present invention provides several novel methods and compositions for identifying agents which alter intermolecular binding between two polypeptide species in a cell or in a cell-free transcription reaction. The invention relates to a general method, referred to herein as a reverse two-hybrid method, wherein agents which disrupt an intermolecular association between two interacting polypeptides thereby generate a selectable and/or detectable readout (e.g., complementation of an auxotrophic phenotype, expression of a detectable reporter molecule, and the like). Typically, a reverse two-hybrid method produces a positive readout under conditions wherein an agent blocks or otherwise inhibits the intermolecular binding of the interacting polypeptides. A positive readout condition is generally identified as one or more of the following detectable conditions: (1) an increased transcription rate of a predetermined reporter gene, (2) an increased concentration or abundance of a polypeptide product encoded by a predetermined reporter gene, typically such as an enzyme which can be readily assayed in vivo, and/or (3) a selectable or otherwise identifiable phenotypic change in an organism (e.g., yeast) harboring the reverse two-hybrid system. Generally, a selectable or otherwise identifiable phenotypic change that characterizes a positive readout condition confers upon the organism either: a selective growth advantage on a defined medium, a mating phenotype, a characteristic morphology or developmental stage, drug resistance, or a detectable enzymatic activity (e.g., β-galactosidase, luciferase, alkaline phosphatase, and the like). In this manner, it is possible to efficiently identify agents (including but not limited to polypeptides, small molecules, and oligonucleotides) which inhibit intermolecular binding between two predetermined interacting polypeptides.

In an aspect of the invention, a reverse two-hybrid system is composed of: (1) a first hybrid protein, (2) a second hybrid protein which binds to the first hybrid protein under control conditions (e.g., physiological conditions in the absence of agent), (3) a relay (or signal inverter) gene which is efficiently expressed as a consequence of the first hybrid protein and the second hybrid protein being functionally bound to each other, and (4) a reporter gene which is efficiently expressed when the product of the relay (or signal inverter) gene is substantially absent and is either poorly expressed or not expressed when the relay (or signal inverter) gene product is efficiently expressed. The first hybrid protein and second hybrid protein bind to each other through interacting polypeptide segments (i.e., a portion of the first hybrid protein preferentially binds to a portion of the second hybrid protein forming a heterodimer or higher order heteromultimer comprising the first and second hybrid proteins; said binding portions of each hybrid protein are termed "interacting polypeptide segments").

The first hybrid protein comprises: (1) a first interacting polypeptide sequence in polypeptide linkage with (2) a DNA-binding domain of a transcriptional activator protein or other DNA binding protein (e.g., a repressor). The second hybrid protein comprises: (1) a second interacting polypeptide sequence, capable of forming an intermolecular association with the first interacting polypeptide sequence under control conditions (e.g., physiological conditions and absence of agent) in polypeptide linkage with (2) an activation domain of a transcriptional activator protein, whereby intermolecular binding between the first hybrid protein and the second hybrid protein (via the interacting polypeptide sequences) thereby unites the DNA-binding domain of the first hybrid protein with the activation domain of the second generating a transcriptional activator function. Generally, the first hybrid protein and the second hybrid protein are encoded by polynucleotides which are constitutively expressed in a host organism (e.g., a eukaryotic or prokaryotic cell, or multicellular organism).

The relay gene (alternatively termed the signal inverter gene) is operably linked to a transcriptional regulatory sequence (a "relay transcriptional regulatory sequence") which is positively regulated by the transcriptional activator that is formed .by the intermolecular binding of the first hybrid protein to the second hybrid protein. Hence, when the first hybrid protein binds to the second hybrid protein (via the interacting polypeptide sequences), the transcriptional activator formed thereby binds to a transcriptional regulatory sequence operably linked to the relay gene and enhances the net transcription of the relay gene. The relay gene encodes a protein that represses transcription of a reporter gene. Thus, when the first and second hybrid proteins are functionally bound to each other, the relay gene is expressed and thereby represses transcription of the reporter gene(s). In an embodiment, such relay proteins are of the type often referred to in the art as "negative regulators of transcription". In an embodiment of the invention, the relay gene is a negative regulator of transcription in yeast; for example but not limitation the GAL80 gene can serve as a relay gene in yeast. In embodiments where host organisms are employed to harbor the reverse two-hybrid system, the relay gene is often a gene which naturally occurs in the germline DNA of the host organism species, and frequently can be an endogenous germline gene, or alternatively may be introduced into the host organism as exogenous DNA, typically into a host genome that lacks the corresponding functional endogenous gene (e.g., a "knockout background").

The reporter gene is operably linked to a transcriptional regulatory sequence ("reporter transcriptional regulatory sequence") which is negatively regulated by the gene product of the relay gene and which is induced in the absence of the relay gene product. Thus, transcription of the reporter gene is repressed in control conditions (e.g., physiological conditions in the absence of agent) wherein the two hybrid proteins bind to each other and form a transcriptional activator that increases transcription of the relay gene. Generally, the relay gene product either binds to the transcriptional regulatory sequence operably linked to the reporter gene, or binds to a transcription protein that binds to the transcriptional regulatory sequence operably linked to the reporter gene. The net transcription rate of the reporter gene is reduced (or completely blocked) as a consequence of the relay gene product binding to the reporter gene transcriptional regulatory sequence and/or to a transcription protein required for constitutive expression of the reporter gene. Any of a variety of reporter genes that produce a positive readout can be used. For example and not limitation, suitable reporter genes are those which (1) confer a selectable phenotype to cells in which the reporter gene is efficiently expressed, and/or (2) encode a gene product (e.g., enzyme) which is conveniently detected such as by in situ assay or the like. Suitable genes which confer a selectable phenotype are exemplified by, but not limited to, genes which complement auxotrophic mutations in a host organism (e.g., yeast HIS3), genes which encode drug resistance (e.g., neo$^R$), genes which induce cell proliferation, and other genes whose expression confers a selective growth advantage. Suitable genes which encode a gene product which is conveniently detected in situ are exemplified by, but not limited to, β-galactosidase (e.g., *E. coli* lacZ), luciferase, alkaline phosphatase, horseradish peroxidase, and the like.

The invention provides polynucleotides encoding a first hybrid protein and a second hybrid protein. Such polynucleotides encode a DNA-binding domain or activation domain of a transcriptional activator and conveniently can have a cloning site for adjacent insertion, in reading frame, of polynucleotide sequences encoding one or more interacting polypeptide sequence(s). Typically, a first polynucleotide will encode a first hybrid protein composed of a first predetermined interacting polypeptide sequence and a DNA-binding domain of a transcriptional activator; a second polynucleotide will encode a second hybrid protein composed of a second predetermined interacting polypeptide sequence and an activation domain of a transcriptional activator, wherein the DNA-binding domain of the first hybrid protein can reconstitute with the activation domain and form a functional transcriptional activator. Often, the DNA-binding domain and the activation domain of the hybrid protein pair are derived from the same naturally occurring transcription activator (e.g., Gal4). However, those of skill in the art can select DNA-binding domains and activation domains from distinct transcription activators which can reconstitute to form a functional transcriptional activator which does not occur in nature (e.g., a DNA-binding domain of the bacterial lexA protein can be used in conjunction with a transcriptional activator from the viral protein, VP16; Vojtek et al. (1993) op.cit.). Transcription and translation of such a polynucleotide produces a hybrid (or fusion) protein composed of an interacting polynucleotide segment and a DNA-binding domain or activation domain of a transcriptional activator.

The invention also provides polynucleotides which comprise a transcriptional regulatory sequence operably linked to a relay (or signal inverter) gene. A relay (or signal inverter) gene encodes a protein that inhibits or otherwise represses expression (typically transcription) of a predetermined reporter gene. Most usually, a relay protein is a negative regulator of transcription for a predetermined gene or gene subset. In an embodiment, the relay protein is a transcription repressor protein that binds to a polynucleotide sequence and thereby inhibits transcription of a cis-linked and operably linked sequence. In an alternative embodiment, the relay protein binds to a protein that is a positive regulator of transcription of a predetermined gene or gene subset, and as a consequence of binding thereby inhibits the transcriptional activity of the positive regulator. One variety of such a relay protein binds to and blocks the activation domain(s) of transcriptional activators. Although a variety of suitable relay proteins are apparent to those of skill in the art, this category of relay protein can be exemplified by the mammalian mdm2 oncoprotein which binds the transactivation domain of the tumor suppressor protein p53, and the yeast Gal80 protein which binds and inactivates the activation domain of Gal4. In an embodiment, the relay protein comprises a mutation, addition, or deletion that reduces the stability of the relay protein in vivo as compared to the naturally occurring cognate relay protein. Relay proteins can be referred to as signal inverter proteins, as they serve to invert a positive transcriptional signal (the reconstitution of a functional transcriptional activator by binding of the two hybrid proteins) into a negative transcriptional signal, which reduces transcription of a predetermined reporter gene. Generally, a polynucleotide encoding a relay protein is operably linked to a relay transcriptional regulatory sequence that produces transcription of the relay gene dependent upon functional reconstitution of the DNA-binding domain and activation domain of the two hybrid proteins. For example and not limitation, such a relay transcriptional regulatory sequence can comprise a promoter and a polynucleotide sequence comprising one or more site(s) which bind(s) a reconstituted functional transcriptional activator formed by association of the two hybrid proteins; for example, if the two hybrid transcriptional activator comprises a lexA DNA-binding domain, the relay transcriptional regulatory sequence operably linked to the relay gene can comprise one or more lexA binding site sequences, arrayed in tandem.

The invention also provides polynucleotides which comprise a transcriptional regulatory sequence operably linked to a reporter gene. The reporter gene encodes a protein that confers a selectable phenotype on a host cell and/or can be detected by an in vivo assay, such as an in situ enzymatic assay (e.g., host cells expressing a lacZ reporter can be detected as blue staining cells in the presence of X-gal). A transcriptional regulatory sequence operably linked to the reporter gene comprises a promoter and generally produces constitutive transcription of the relay gene contingent upon the substantial absence of the relay protein. In an embodiment, the reporter transcriptional regulatory sequence operably linked to the reporter gene comprises a binding site for a relay protein, wherein binding of the relay protein to the reporter transcriptional regulatory sequence inhibits constitutive transcription of the reporter gene. In an alternative embodiment, the reporter transcriptional regulatory sequence linked to the reporter gene comprises a binding site for a transcriptional activator protein, wherein binding of a constitutive transcriptional activator protein to the reporter transcriptional regulatory sequence produces constitutive transcription of the cis-linked reporter gene, and wherein the relay protein binds to or otherwise inactivates the transcriptional activator protein, thereby repressing constitutive expression of the reporter gene.

The invention also provides host organisms (typically unicellular organisms) which harbor a reverse two-hybrid system, typically in the form of polynucleotides encoding a first hybrid protein, a second hybrid protein, a relay gene, and/or a reporter gene, wherein said polynucleotide(s) are either stably replicated or introduced for transient expression. In an embodiment, the host organism is a yeast cell (e.g., *Saccharomyces cervisiae*) in which the germline GAL80 gene is functionally inactivated, the relay gene encodes Gal80, and the reporter gene transcriptional regulatory sequence comprises a Gal4-responsive promoter.

The invention also provides a method for identifying agents that inhibit binding of a first interacting polypeptide to a second interacting polypeptide. The method employs the reverse two-hybrid system described supra, wherein a first hybrid protein comprises the first interacting polypeptide and a second hybrid protein comprises a second interacting polypeptide. Heterodimerization (or higher order heteromultimerization) between the first hybrid protein and the second hybrid protein produces transcription of a relay gene encoding a protein which inhibits expression of a reporter protein. Host organisms harboring such a reverse two-hybrid system are cultured in the presence of an agent, such as a diffusible small molecule (typical MW<5,000, preferably <1,000) or a transfected cDNA expression polynucleotide encoding a polypeptide agent, and expression of the host organism reporter gene is determined and standardized to a parallel blank culture which lacks an agent. Agents which produce a significant increase in expression of the reporter gene in a host organism after a suitable time period (e.g., usually at least 1 hour, often at least 3 hours, preferably about 6 hours, occasionally overnight or longer) are thereby identified as inhibitors for blocking the intermolecular association between the first an second interacting polypeptide sequences. Such protein interaction inhibitors are candidate drugs for pharmaceutical use and/or for use as commercial research reagents. In an embodiment of the invention, yeast cells are the host organism, the reporter gene encodes β-galactosidase and/or a protein that complements an auxotrophic mutant yeast host cell, and the first and second interacting polypeptide sequences each comprise a binding domain derived from a signal transduction protein.

The invention also provides a kit comprising a reverse two-hybrid system, a host cell, and an instruction manual. Such kits may optionally include a panel of agents for testing.

DETAILED DESCRIPTION

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is-the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "agent" is used herein to denote a chemical compound, a mixture of chemical compounds, a biological macromolecule, or an extract made from biological materials such as bacteria, plants, fungi, or animal (particularly mammalian) cells or tissues. Agents are evaluated for potential activity as specific protein interaction inhibitors (i.e., an agent which selectively inhibits a binding interaction between two predetermined polypeptides but which does not substantially interfere with cell viability) by inclusion in screening assays described hereinbelow.

The term "protein interaction inhibitor" is used herein to refer to an agent which is identified by one or more screening method(s) of the invention as an agent which selectively inhibits protein-protein binding between a first interacting polypeptide and a second interacting polypeptide. Some protein interaction inhibitors may have therapeutic potential as drugs for human use and/or may serve as commercial reagents for laboratory research or bioprocess control. Protein interaction inhibitors which are candidate drugs are then tested further for activity in assays which are routinely used to predict suitability for use as human and veterinary drugs, including in vivo administration to non-human animals and often including administration to human in approved clinical trials.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

As used herein, the term "endogenous DNA sequence" refers to naturally-occurring polynucleotide sequences contained in a eukaryotic or prokaryotic cell. Such sequences include, for example, chromosomal sequences (e.g., structural genes, promoters, enhancers, recombinatorial hotspots, repeat sequences, integrated proviral sequences). A "predetermined sequence" is a sequence which is selected at the discretion of the practitioner on the basis of known or predicted sequence information. An exogenous polynucleotide is a polynucleotide which is transferred into a eukaryotic or prokaryotic cell.

As used herein the term "physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50–200 mM NaCl or KCl, pH 6.5–8.5, 20°–45° C. and 0.01–10 mM divalent cation (e.g., $Mg^{++}$, $Ca^{++}$); preferably about 150 mM NaCl or KCl, pH 7.2–7.6, 5 mM divalent cation, and often include 0.01–1.0 percent nonspecific protein (e.g., BSA). Particular aqueous conditions may be selected by the practitioner according to conventional methods. For general guidance, the following buffered aqueous conditions may be applicable: 10–250 mM NaCl, 5–50 mM Tris HCl, pH 5–8, with optional addition of divalent cation(s) and/or metal chelators and/or nonionic detergents and/or membrane fractions.

The terms "functional disruption" or "functionally disrupted" as used herein means that a gene locus comprises at least one mutation or structural alteration such that the functionally disrupted gene is substantially incapable of directing the efficient expression of functional gene product.

As used herein, the terms "interacting polypeptide segment" and "interacting polypeptide sequence" refer to a portion of a hybrid protein which can form a specific binding interaction with a portion of a second hybrid protein under suitable binding conditions. Generally, a portion of the first hybrid protein preferentially binds to a portion of the second hybrid protein forming a heterodimer or higher order heteromultimer comprising the first and second hybrid proteins; the binding portions of each hybrid protein are termed interacting polypeptide segments.

DESCRIPTION OF THE INVENTION

Generally, the nomenclature used hereafter and the laboratory procedures in cell culture, molecular genetics, and nucleic acid chemistry and cell culture described below are those well known and commonly employed in the art. Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y., which is incorporated herein by reference) which are provided throughout this document. The procedures therein are believed to be well known in the art and are provided for the convenience of the reader. All the information contained therein is incorporated herein by reference.

The reverse two-hybrid method is generally applicable for identifying agents which inhibit binding between a variety of predetermined interacting polypeptides.

Overview

A basis of the present invention is a strategy for screening a bank of agents with a reverse two-hybrid system to identify agents which inhibit the intermolecular association of two interacting polypeptide sequences. Thus, in a reverse two-hybrid system there is at least one pair of interacting polypeptide sequences, with a first interacting polypeptide sequence present in one of the hybrid protein species and a second interacting polypeptide sequence present in the other hybrid protein species. The choice of interacting polypeptide sequences incorporated in a reverse two-hybrid system is selected at the discretion of the practitioner. For example, a reverse two-hybrid system suitable for identifying agents which inhibit Fos/Jun leucine zipper formation may be composed of a first hybrid protein having an interacting polypeptide sequence comprising a Fos leucine zipper and a second hybrid protein having an interacting polypeptide sequence comprising a Jun leucine zipper. A variety of interacting protein sequences can be used; for example and not limitation, these include: transcription factor binding domains, multisubunit proteins, signal transduction proteins (G proteins, members of ras/raf/MEK signaling pathway(s), tumor suppressor protein binding domains (Rb, p53), and the like), polypeptide ligands and their cognate receptor(s), active sites of enzymes which catalyze reactions involving binding to a polypeptide substrate and the polypeptide substrate itself, and essentially any pair of protein sequences which form an intermolecular association under physiological conditions. Generally, interacting polypeptides form heterodimers with a dissociation constant ($K_D$) of at least about $1\times10^3$ $M^{-1}$, usually at least $1\times10^4$ $M^{-1}$, typically at least $1\times10^5$ $M^{-1}$, preferably at least $1\times10^6$ $M^{-1}$ to $1\times10^7$ $M^{-1}$ or more, under suitable physiological conditions.

Reverse two-hybrid systems are used for detecting the ability of agents to inhibit the intermolecular binding of two interacting polypeptides and provide for facile high-throughput screening of agent banks (e.g., compound libraries, peptide expression libraries, and the like) to identify protein interaction inhibitors which preferentially inhibit intermolecular binding between two predetermined interacting polypeptide species. Such protein interaction inhibitors (specific binding antagonists) can modulate biochemical activity of the predetermined interacting specie(s) and thereby modulate biological function. Agents which alter the intermolecular association of the two interacting polypeptide sequences in the hybrid proteins, generally by inhibiting heterodimeric binding of the two hybrid proteins, score positively in the reverse two-hybrid system. The protein interaction inhibitors thereby identified are candidate drugs for human and veterinary therapeutic use and/or are suitable commercial reagents for laboratory research or bioprocess control.

An agent capable of specifically inhibiting protein-protein binding of a therapeutically relevant protein interaction in vivo can be used for therapy of disease or for modulation of gene expression in cells and organisms. Typically, an efficacious dose of a protein interaction inhibitor is administered to a patient as a therapeutic or prophylactic for treating a pathological condition (e.g., cancer, inflammation, lymphoproliferative diseases, autoimmune disease, and the like).

DESCRIPTION OF THE PREFERRED EMBODIMENT

In order to illustrate the invention, a description of a preferred embodiment is presented below. This embodiment comprises a reverse two-hybrid system in yeast cells that are functionally disrupted for endogenous GAL80 expression, wherein the intermolecular association of the first and second hybrid proteins activates transcription of a GAL80 relay gene. Expression of GAL80 represses the transcriptional activity of constitutively expressed Gal4 protein and inhibits transcription of a Gal4-dependent reporter gene.

A variety of alternative embodiments and variations will be apparent to those of skill in the art, including alternative relay genes, alternative host cells (e.g., mammalian, bacterial, fungal, insect, and the like), variations of the basic reverse two-hybrid method, and others.

Two-Hybrid systems

Transcriptional activators are proteins that positively regulate the expression of specific genes. They can be functionally dissected into two structural domains: one region that binds to specific DNA sequences and thereby confers specificity, and another region termed the activation domain that binds to protein components of the basal gene expression machinery (Ma and Ptashne (1988) Cell 55: 443). These two domains need to be physically connected in order to function as a transcriptional activator. Two-hybrid systems exploit this finding by hooking up an isolated DNA binding domain to one protein (protein X), while hooking up the isolated activation domain to another protein (protein Y). When X and Y interact to a significant extent, the DNA binding and activation domains will now be connected and the transcriptional activator function reconstituted (Fields and Song (1989) *Nature* 340: 245). The yeast host strain is engineered so that the reconstituted transcriptional activator drives the expression of a specific reporter gene such as HIS3 or lacZ, which provides the read-out for the protein-protein interaction (Field and Song (1989) op.cit.; Chein et al. (1991) op.cit.). One advantage of two-hybrid systems for monitoring protein-protein interactions is their sensitivity in detection of physically weak, but physiologically important, protein-protein interactions. As such it offers a significant advantage over other methods for detecting protein-protein interactions (e.g., ELISA assay). Unlike the ELISA assay, however, the current two-hybrid system is not readily transplantable to drug screening operations. A major problem with the existing two-hybrid methods is that nonspecific inhibitors of transcriptional activation score the same as inhibitors of the specific protein-protein interaction.

Negative Regulators of Transcription

To address the aforementioned problem, the read-out of the conventional two-hybrid interaction can be reversed by interposition of a relay gene which serves to invert the output produced from interaction of the two hybrid proteins from a positive transcriptional activator to a negative transcriptional regulator (e.g., repressor). In order to invert the readout from a positive transcription activator to a negative transcription repressor, it is possible to take advantage of the properties of certain negative regulators of transcription. In an embodiment, some of these negative regulators block the function of specific transcriptional activators by binding to their activation domain. Two such examples are the mdm2 oncoprotein which binds to and masks the trans-activation domain of the tumor suppressor protein p53 (Momand et al. (1993) *Cell* 69: 1237; Oliner et al. (1993) *Nature* 362: 857), and the yeast Gal80 protein which binds and inactivates the transcriptional activator region of Gal4 (Ma and Ptashne (1987) *Cell* 50: 137; Johnston and Carlson (1993) *Regulation of Carbon and Phosphate Metabolism*, vol. 2, Cold Spring Harbor Press, Cold Spring Harbor, N.Y.). By designing the two-hybrid interaction to drive the expression of a negative regulator of a specific transcriptional activator, the resultant system is such that interference with the two-hybrid interaction results in increased activity of a transcriptional activator and hence a positive signal. In view of the fact that the biology of the Gal80-Gal4 system is well understood in yeast, this pair of negative-regulators/transcriptional activators is suitable for the reverse two-hybrid method. In principle, the pair of mdm2 and p53 proteins, or any other matched pair of transcriptional activator and specific negative regulator, will also work.

In the present embodiment, the two interacting hybrid proteins reconstitute a transcriptional activator composed of a DNA binding domain derived from the bacterial protein encoded by lexA and an activator domain derived from the viral protein VP16 (Vojtek et al. (1993) op.cit.). The reconstituted lexA/VP16 transcriptional activator binds to a relay gene operably linked to a transcriptional regulatory sequence containing tandem copies of a lexO binding site sequence which binds the lexA DNA-binding domain. Upon binding of the reconstituted lexA/VP16 transcriptional activator to the lexO binding site(s), the operably linked relay gene (GAL80) is efficiently expressed. Thus, when the two hybrid proteins are associated (e.g., as a heterodimer or the like), the GAL80 relay gene is expressed and serves to repress expression of a reporter gene construct.

The Gal80–Gal4 System

The Gal80–Gal4 system of regulatory proteins underlies the ability of yeast cells to respond to exogenously added galactose and specifically synthesize the enzymes needed to utilize it as a carbon/energy source (Johnston and Carlson (1993) op.cit.. Unless galactose is present, the Gal80 protein binds and blocks the function of the transcriptional activator Gal4. In the absence of the GAL80 gene, the transcriptional activator function of Gal4 is not masked and hence expression of galactose-regulated genes no longer requires galactose for induction. In the reverse two-hybrid system, the host strain generally is functionally disrupted for the endogenous GAL80 gene, but Gal80 protein is provided through a two-hybrid driven relay gene construct (see, Experimental Example, infra) which is operably linked to a transcriptional regulatory sequence that binds a bacterial lexA DNA-binding domain present in the first hybrid protein. When the two-hybrid interaction is driving the expression of the relay gene product, Gal80, the Gal4-induction of the reporter gene(s) is inhibited. When the two-hybrid interaction is blocked, the relay gene (GAL80) expression will be turned off and the Gal4-dependent transcriptional regulatory sequence operably linked to the reporter gene(s) is then able to drive expression of the reporter gene(s).

Techniques for Fine-Tuning Expression of the Relay Gene

The sensitivity of this system can be modulated by adjusting the amount of Gal4 or Gal80 protein. A host strain generally contains the wild-type GAL4 gene and hence contains very low levels of Gal4 when the yeast cells are cultured with carbon/energy sources such as raffinose (Johnston and Carlson (1993) op.cit.). If necessary, the level of Gal4 protein can be decreased by at least five-fold by culturing the cells in glucose (Griggs and Johnston (1991) *Proc. Natl. Acad. Sci.* (USA) 88: 8597). Higher levels of Gal4 protein can be provided by transforming the strain with a multicopy plasmid encoding Gal4 (Schultz et al. (1987).

The amount and/or stability of the relay protein, Gal80, can also be adjusted. Preferably, the stability of the Gal80 protein is sufficient such that the addition of protein interaction inhibitor agents generates a detectable readout of the reporter gene(s) within about six hours, or most usually within the time-frame of an overnight assay. For this to be a convenient assay approach, Gal80 activity preferably deteriorates at a rapid rate when active inhibitor agents are added and the two-hybrid system is inhibited. The half-life of Gal80 proteins in yeast cells has not been rigorously defined in the art. If Gal80 has a short half-life, it is generally only necessary to vary the level of transcription of GAL80 by changing either copy number of the two-hybrid relay gene construct or by varying the number of binding sites for the transcriptional activator (e.g., lexO operator sequences) in the transcriptional regulatory sequence of the relay gene construct. If Gal80 has an inordinately long half-life, it is preferable to engineer a chimeric Gal80 protein with a shorter half-life. Successful engineering of long-lived proteins to proteins with shorter half-lives has been achieved by addition of PEST sequences to DHFR (Loetscher et al. (1991) *J. Biol. Chem.* 266:11213) or by forming β-galactosidase variants with different N-terminal residues by in vivo processing of ubiquitin-β-galactosidase fusions (Varshavsky et al. (1989) *Yeast Genetic Engineering,* Barr, Brake, and Valenzuela (eds.), Butterworths, pp. 109–143). The latter method has been well characterized in yeast, such that Gal80 variants with half-lives ranging from 2 minutes to over 24 hours can be readily generated.

The following examples are offered by way of example and not by way of limitation.

EXPERIMENTAL EXAMPLES

Construction of the appropriate host yeast strains

Since the GAL80–GAL4 system is employed, the reporter genes in the yeast strain need to be operably linked to promoters that are responsive to Gal4. Reporter genes that have been operably linked to Gal4-responsive promoters were integrated into yeast strains (see Construction of Yeast Strains, infra). One of the reporter genes encodes β-galactosidase, whose expression allows quantitative transcriptional read-out, if desired. It is possible to utilize other reporter genes operably linked to Gal4responsive promoters, such as ones encoding alkaline phosphatase, that would also allow easy quantitation of transcriptional read-out. JEY8, JEY10, and JEY12, three independent progenitors for the reverse-two hybrid host strains, were derived by standard genetic methods from a cross between YM2170 (MATa ura3 his3 ade2 lys2 tyr1 GAL4$^+$ gal80Δ LEU2:GAL1-lacZ; available from Dr. Mark Johnston, Washington University, St. Louis, Mo.) and YPB2 (MATa his3 ade2 leu2 ura3 lys2 trp1 can1 gal4Δ gal80Δ LYS2::GAL1-HIS3 URA3::GAL1-lacZ) (Bartel et al. (1993) in *Cellular Interactions in Development: A Practical Approach,* Hartley DA (ed.) Oxford University Press, Oxford, UK, pp. 153). The progenitor strains (MATa his3 ade2 leu2 ura3 lys2 trp1 GAL4$^+$ gal80Δ LYS2::GAL1-HIS3 URA3::GAL1-lacZ) contain all the necessary reporter genes and have been tested for a functional Gal4 protein and reporter genes by analysis of galactose-induced expression of β-galactosidase. To test in general whether re-introduction of Gal80 protein negatively regulates Gal4 in the system, JEY8 was transformed with a high-copy plasmid containing the wild-type GAL80 gene (pBM260; available from Mark Johnston, Washington University, St. Louis, Mo.). Sufficient expression results in inhibition of the read-outs from the reporter genes (HIS3 and lacZ), which are determined by assaying β-galactosidase activity and growth in the absence of histidine. Both of these reporter activities are scored in yeast grown on plates containing raffinose (which allows for full activity of Gal80 protein) and galactose (which inactivates Gal80 protein). These tests confirm that in these strains the Gal80 protein, expressed off its endogenous promoter, suppresses Gal4 function. Two-hybrid constructs are evaluated for their ability to drive sufficient GAL80 expression from the LexO-GAL80 fusion plasmids that are constructed (see, infra).

Construction of the LexO-GAL80 fusion genes

A chimeric gene (a LexO-GAL80 fusion) is constructed and serves as the relay (signal inverter) gene. The DNA-binding domain of the transcriptional activator that is used to drive expression of the relay gene is derived from the bacterial protein encoded by lexA and has been used before in two-hybrid systems as a fusion with the transcriptional activator from the viral protein VP16 (Vojtek et al. (1993) op.cit.. Other transcriptional activators that have a defined DNA binding site, such as the ACE1 gene product of *S. cerevisiae* (Munder and Furst (1992) *Mol. Cell. Biol.* 12: 2091) may be used. The LexO sites are generated by mutually primed synthesis (see. Chapter 8.2A in *Current Protocols in Molecular Biology* (1990) Ausubel, Brent, Kingston, Moore, Seidman, Smith, and Struhl (eds.), Greene Publishing Associates and Wiley Interscience, New York, N.Y.) using the oligomer 5'-GCGAATTCCTACTG-TATATACATACAGTACCATCTACTG-TATATACATACAGTAGC CGCTCGAGCGGC-3'[SEQ ID NO:1]. The resulting fragment contains four consensus LexA binding sites in tandem. The DNA product is digested with EcoRI and inserted into the EcoRI site of pCZD (Lue et al. (1989) *Proc. Natl. Acad. Sci. (USA)* 86: 486) to generate pCZD-LexO. The pCZD vector contains a minimal TATA box for recognition of the basal transcriptional machinery but requires the addition of specific DNA sequences to effectively function as promoter box. The Gal80 coding sequence is isolated by PCR using the following two oligomers: 5'-CGCGGATCCCGTTCTTTC-CAC TCCCG-3'[SEQ ID NO:2]; and 5'-CGGATCCGATG-GAAGGATGCCCGCTGCTGC-3'[SEQ ID NO: 3]. The template is the plasmid pBM260 which contains the GAL80 gene subcloned in YEp13 (available from Mark Johnston, Washington University, St. Louis, Mo.). The GAL80 PCR product is digested with BamHI and inserted into the BamHI site of pCZD-LexO to create pLexO-Gal80. The LexO-Gal80 fusion is then subcloned into pGalileo, a 2μ based yeast shuttle vector (20–30 copies per cell) carrying the ADE2 selectable marker(available from Avtar Roopra, Washington University, St. Louis, Mo.) to generate pJE42. From this plasmid, CEN- and integrating versions are constructed to provide a means of controlling the level of expression of GAL80 by the two-hybrid interaction. For example, the basal transcription from the 2μ plasmid may express sufficient Gal80 to require galactose for expression of the reporter gene(s) even in the absence of a lexA-based transcriptional activator. Additionally, LexO-ubiquitin-Gal80 fusions encoding a shortened half-life Gal80 protein is constructed.

In order to demonstrate that relay gene constructs comprising a LexO-GAL80 polynucleotide fusion can be activated by the two-hybrid interaction to sufficient levels for regulating the Gal4-mediated reporter gene expression, a positive control is generated. Yeast are transformed with a plasmid that contains a fusion of the DNA binding domain (lexA) and transcriptional activation component (VP16) of the two-hybrid system and activates transcription of the relay gene LexO-GAL80 fusion. The plasmid pLEX-VP16 (available from A. Vojtek; Vojtek et al. (1993) op.cit.) is used for the positive control. The ability of two-hybrid interactions to drive expression of the relay gene is demonstrated.

Testing for the ability of two-hybrid interactions to drive expression of the LexO-GAL80 fusions The two-hybrid interaction that is used to test for its ability to drive sufficient expression of the LexO-GAL80 relay gene is the interaction of human H-ras p21 with human c-Raf (Van Aelst et al. (1993) *Proc. Natl. Acad. Sci. (USA)* 90: 6213; Vojtek et al. (1993) op.cit.). K-ras is linked by in-frame polynucleotide fusion to the VP16 activation domain, and Raf is linked by in-frame polynucleotide fusion to the DNA binding domain of the lexA gene product. pGBT8-Raf was constructed by ligating EcoRI and PstI linkers to a Raf coding sequence isolated by PCR amplification of a human placental cDNA library from Stratagene (San Diego, Cal.) as described by MacDonald et al. (1993)

*Mol. Cell. Biol.* 13: 6615. The Raf gene was cut out of pGBT8-Raf as an EcoRI to PstI fragment and subcloned into the EcoRI-PstI site of pBTM116 (that contains the LexA DNA binding domain (Vojtek et al. (1993) op.cit.) to generate pBTM-Raf (pJE36). The EcoRI site maintains the same reading frame. pGBT8K-ras was constructed by PCR amplification of pEXV-K-ras (Hancock et al. (1990) *Cell* 63: 133) such that the K-ras sequence is isolated as a SalI-PstI restriction fragment which was then subcloned into SalI-PstI-cut pGBT8. To construct pVPK-ras (pJE44), a PCR product of pGBT8K-ras was generated using the following oligomers as PCR amplimers:
5'-CGGGATCCATGACTGAATATAAACTTGTGGTAG-3' [SEQ ID NO:4]
5'-CGGGATCCTTACATAATTACA-CACTTTGTCTTTCACTTG-3' [SEQ ID NO:5] and the resultant PCR product was digested with BamHI and subcloned into the BamHI site of pVP16 (Vojtek et al. (1993) op.cit.) to generate pVPK-ras (pJE44). The LexO-GAL80 relay gene plasmid, the pBTM-Raf and the pVP-K-ras (pJE44) plasmids are cotransfected into a host yeast strain and the ability of the two-hybrid interaction to drive sufficient expression of GAL80 to prevent the expression of the reporter genes (lacZ and HIS3) is determined. Growth on galactose is used as an internal positive control to ensure that the promoter is still functional.

Testing for the ability of a small molecule to interfere with a two-hybrid interaction The reverse two-hybrid method is used as a screening assay for identifying small molecule inhibitors of protein-protein interaction, such that an exogenously added small molecule can interfere with a two-hybrid interaction. In one example, a reverse two-hybrid system utilizes the small molecule estradiol as the protein interaction inhibitor. Estradiol is a small lipophilic molecule that has been shown to be effective in yeast. It has been shown that estradiol reverses the interaction of the hormone binding domain of the estrogen receptor with the heat-shock protein HSP90. Thus, a first hybrid protein comprising the hormone binding domain of the estrogen receptor in polypeptide linkage to a lexA DNA-binding domain and a second hybrid protein comprising the heat shock protein, HSP90, in polypeptide linkage to the VP16 activation domain are constructed by standard methods. Polynucleotide(s) encoding the first and second hybrid proteins, a LexO-GAL80 relay gene construct, and a Gal4-dependent reporter gene construct are introduced into the yeast host. Estrogen (e.g., estradiol) is evaluated as an agent for inhibiting formation of a functional two-hybrid heterodimer and thereby producing expression of the reporter gene.

Testing for the ability of a polypeptide to interfere with a two-hybrid interaction The reverse two-hybrid method is used as a screening assay for identifying polypeptide inhibitors of protein-protein interaction, such that an intracellularly expressed polypeptide can interfere with a two-hybrid interaction. In one embodiment, a reverse two-hybrid system utilizes a polypeptide expressed from a cotransfected cDNA expression construct as the protein interaction inhibitor.

A first hybrid protein comprising a first interacting polypeptide sequence in polypeptide linkage to a lexA DNA-binding domain and a second hybrid protein comprising a second interacting polypeptide sequence in polypeptide linkage to the VP16 activation domain are constructed by standard methods. Polynucleotide(s) encoding the first and second hybrid proteins, a LexO-GAL80 relay gene construct, and a Gal4-dependent reporter gene construct are introduced into the yeast host. A polynucleotide encoding and expressing a polypeptide typically between 5 and 500 amino acids long (e.g., a library member of a cDNA expression library) is also introduced into the yeast cells under conditions wherein the encoded polypeptide is expressed intracellularly. The expressed polypeptide is evaluated as an agent for inhibiting formation of a functional two-hybrid heterodimer and thereby producing expression of the reporter gene.

Essentially any of various expression clone libraries known in the art may be used, including commercially available expression libraries (Clontech, Inc., Palo Alto, Cal.). Expression clone libraries may also be generated by the practitioner by conventional cloning methods and vectors known in the art (e.g., pcD, pSV), especially yeast expression vectors. Expression clone libraries comprise a collection of library members, each member comprising a cloned polynucleotide sequence (which may comprise mutation(s) or deletions), typically a cDNA sequence, operably linked to a promoter (and optionally an enhancer) which is transcriptionally active in the host cell so that the cloned sequence is transcribed and translated into a polypeptide. Genomic DNA sequences (e.g., complete structural genes or fragments thereof) may also serve as cloned sequences in expression libraries. Preferably, the cloned sequence is inserted in cloning site which facilitates the recovery of the cloned sequence free from the promoter and other sequences which comprise an expression cassette.

Expression clone library members are transferred into host cells by various means, including but not limited to: electroporation, lipofection, viral vector transduction, biolistics, and $CaPO_4$ precipitation. Expression clone library members may be transferred directly into host cells, or a relay and/or reporter polynucleotide and/or polynucleotide(s) encoding the first and second hybrid proteins may be cotransferred with expression clone library members into a host cell, or a relay and/or reporter polynucleotide and/or polynucleotide(s) encoding the first and second hybrid proteins may be transferred into host cells subsequent to transfer of expression clone library members.

Cloned polynucleotides can be recovered from expression clone library members which are isolated by the screening methods of the invention. Typically, cloned sequences are excised by restriction digestion with an enzyme(s) which cleave at the boundaries between the ends of the cloned sequence (e.g., cDNA) and the remainder of the expression clone library member. Alternatively, PCR (preferably high-fidelity PCR) or other amplification method (e.g., LCR) may be performed using primers which flank the site at which the cloned sequence is inserted in the library member to amplify and thereby isolate the cloned sequence (U.S. Pat. No. 4,683,202, incorporated herein by reference). When PCR is used, it is generally preferable to incorporate known unique polynucleotide sequences flanking at least one, and preferably both, side(s) of the site in which a cloned sequence is inserted to facilitate recovery of the selected cloned sequence(s).

Although the present invention has been described in some detail by way of illustration for purposes of clarity of understanding, it will be apparent that certain changes and modifications may be practiced within the scope of the claims.

We claim:

1. A reverse two-hybrid system comprising:
   (1) a first hybrid protein comprising a first interacting polypeptide sequence in polypeptide linkage to a DNA-binding domain of a transcriptional activator;
   (2) a second hybrid protein comprising a second interacting polypeptide sequence in polypepfide linkage to an activation domain of a transcriptional activator, wherein the second hybrid protein binds to the first hybrid protein via contact of the interacting polynucleotide sequences under physiological conditions;
   (3) a relay gene whose transcription is dependent upon the first hybrid protein and the second hybrid protein being bound to each other, thereby reconstituting a transcriptional activator, said relay gene encoding Gal80 operably linked to a LexO sequence in a cis-linked relay gene transcription regulatory sequence;
   (4) a reporter gene whose transcription is repressed by expression of the relay gene and which is substantially transcribed in the absence of relay gene expression; said reporter gene operably linked to a transcription regulatory sequence which confers Gal4-dependent transcription to cis-linked adjacent polynucleotide sequences; and
   (5) a Saccharomyces host cell.

2. A reverse two-hybrid system of claim 1, wherein
   the first hybrid protein comprises a lexA DNA-binding domain in polypeptide linkage to the first interacting polypeptide sequence;
   the second hybrid protein comprises a VP16 activation domain in polypeptide linkage to the second interacting polypeptide sequence;
   the relay gene encodes Gal80 operably linked to a LexO sequence in a cis-linked relay gene transcription regulatory sequence; and
   the reporter gene comprises lacZ or HIS3 and is operably linked to a transcription regulatory sequence which confers Gal4-dependent transcription to cis-linked adjacent polynucleotide sequences.

3. A reverse two-hybrid system of claim 2 in a yeast cell produced by crossing a Saccharomyces organism having the genotype MATa his3 ade2 leu2 ura3 lys2 trp1 GAL4$^+$ gal80D LYS2::GAL1-HIS3 URA3::GAL1-lacZ.

4. A reverse two-hybrid system of claim 2 further comprises an expression clone library member which expresses an intracellular polypeptide in the Saccharomyces host cell.

5. A kit comprising a reverse two-hybrid system of claim 2, an instruction manual, and optionally a panel of agents for testing.

6. A reverse two-hybrid system of claim 2, wherein the first interacting polypeptide sequence is a mammalian ras polypeptide and the second interacting polypeptide sequence is a Raf polypeptide.

7. A polynucleotide encoding a Gal80 polypeptide and comprising at least one operably linked LexO binding site.

8. A polynucleotide of claim 7 in a yeast cell which contains a functionally disrupted endogenous GAL80 gene.

9. A Saccharomyces host cell containing said two-hybrid system of claim 1, and further comprising an agent having a molecular weight of less than 1,000 daltons.

10. A Saccharomyces host cell of claim 9, further comprising an expression clone library member which expresses a polypeptide encoded by a cDNA.

11. A method for identifying agents which inhibit intermolecular binding under physiological conditions between a first interacting polypeptide sequence and a second interacting polypeptide sequence, said method comprising the steps of:

administering an agent to a Saccharomyces host cell containing a reverse two-hybrid system of claim 1 and incubating the host cell for a suitable period;

determining whether the administration of the agent induces a substantial expression of the reporter gene; and identifying an agent which induces a substantial expression of the reporter gene as a protein interaction inhibitor.

12. A method of claim 11, wherein the agent is a molecule having a molecular weight less than about 1,000 daltons.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_feature
        ( B ) LOCATION: 1..68
        ( D ) OTHER INFORMATION: /standard_name="PCR primer"

( x i ) SEQUENCE DESCRIPTION: SEQ ID NO:1:

```
GCGAATTCCT ACTGTATATA CATACAGTAC CATCTACTGT ATATACATAC AGTAGCCGCT      60
CGAGCGGC                                                               68
```

( 2 ) INFORMATION FOR SEQ ID NO:2:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_feature
        ( B ) LOCATION: 1..26
        ( D ) OTHER INFORMATION: /standard_name="PCR primer"

( x i ) SEQUENCE DESCRIPTION: SEQ ID NO:2:

```
CGCGGATCCC GTTCTTTCCA CTCCCG                                           26
```

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_feature
        ( B ) LOCATION: 1..30
        ( D ) OTHER INFORMATION: /standard_name="PCR primer"

( x i ) SEQUENCE DESCRIPTION: SEQ ID NO:3:

```
CGGATCCGAT GGAAGGATGC CCGCTGCTGC                                       30
```

( 2 ) INFORMATION FOR SEQ ID NO:4:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( i x ) FEATURE:
( A ) NAME/KEY: misc_feature
( B ) LOCATION: 1..33
( D ) OTHER INFORMATION: /standard_name="oligomer for PCR"

( x i ) SEQUENCE DESCRIPTION: SEQ ID NO:4:

CGGGATCCAT GACTGAATAT AAACTTGTGG TAG     33

( 2 ) INFORMATION FOR SEQ ID NO:5:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( i x ) FEATURE:
( A ) NAME/KEY: misc_feature
( B ) LOCATION: 1..39
( D ) OTHER INFORMATION: /standard_name="oligomer for PCR"

( x i ) SEQUENCE DESCRIPTION: SEQ ID NO:5:

CGGGATCCTT ACATAATTAC ACACTTTGTC TTTCACTTG     39